(12) United States Patent
Ehrichs et al.

(10) Patent No.: US 6,401,008 B1
(45) Date of Patent: Jun. 4, 2002

(54) SEMICONDUCTOR WAFER REVIEW SYSTEM AND METHOD

(75) Inventors: Edward E. Ehrichs; Chris Wooten, both of Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/195,300

(22) Filed: Nov. 18, 1998

(51) Int. Cl.[7] .................................................. G06F 7/00
(52) U.S. Cl. ...................... 700/228; 700/213; 324/158.1
(58) Field of Search ................................. 700/213, 228, 700/110; 324/765, 158.1; 348/92; 438/14, 16

(56) References Cited

U.S. PATENT DOCUMENTS

| | | | |
|---|---|---|---|
| 4,618,938 A | 10/1986 | Sandland et al. | |
| 4,775,281 A | 10/1988 | Prentakis | |
| 4,856,904 A | 8/1989 | Akagawa | |
| 4,938,654 A | 7/1990 | Schram | |
| 5,096,291 A | 3/1992 | Scott | |
| 5,105,147 A | 4/1992 | Karasikov et al. | |
| 5,324,012 A | 6/1994 | Aoyama et al. | |
| 5,493,236 A | * 2/1996 | Ishii et al. .................... | 324/752 |
| 5,578,821 A | 11/1996 | Meisberger et al. | |
| 5,640,237 A | 6/1997 | Esrig et al. | |
| 5,647,718 A | 7/1997 | Weisler et al. | |
| 5,765,890 A | 6/1998 | Gaylord et al. | |
| 5,847,821 A | * 12/1998 | Tracy et al. .................. | 356/237 |
| 5,923,430 A | * 7/1999 | Worster et al. .............. | 356/394 |
| 5,955,877 A | * 9/1999 | Farnworth et al. ........ | 324/158.1 |
| 5,959,461 A | * 9/1999 | Brown et al. ................ | 324/765 |
| 5,963,314 A | * 10/1999 | Worster et al. .......... | 356/237.2 |

* cited by examiner

Primary Examiner—Joseph E. Valenza
Assistant Examiner—Khoi H. Tran (57) ABSTRACT

A semiconductor wafer review system and method. A method and system for front and back side review of semiconductor wafers is provided in various embodiments. Inspection data for the front side is used to position the wafer for front side review, and a wafer inverter is provided to flip the wafer for back side review. Inspection data for the back side is used to position the wafer for back side review.

29 Claims, 10 Drawing Sheets

SEMICONDUCTOR WAFER REVIEW SYSTEM AND METHOD

RELATED PATENT APPLICATIONS

The present patent application is related to co-pending patent application, entitled, "SEMICONDUCTOR WAFER ANALYSIS SYSTEM AND METHOD," by Ehrichs and Wooten, now U.S. Pat. No. 6,156,580 issued Dec. 15, 2000, filed concurrent herewith, and assigned to the assignee of the present invention, the contents of which is hereby incorporated by reference.

FIELD OF THE INVENTION

The present invention is directed generally to semiconductor defect analysis, and more particularly to systems and method for review of semiconductor wafers.

BACKGROUND OF THE INVENTION

Over the last few decades, the electronics industry has undergone a revolution by the use of semiconductor technology to fabricate small, highly integrated electronic devices. The most common semiconductor technology presently used is silicon-based. A large variety of semiconductor devices have been manufactured having various applicability and numerous disciplines.

In-line inspection and review are important for determining whether wafers have become contaminated with particles due to a tool malfunction or process problem. Contamination can lead to reduced yield. The "inspection" of a wafer generally includes scanning the wafer with a laser and recording positions at which defects or particles deflect the laser. The positions are then used for "review" of the wafer with a microscope. Inspection and review often take place at separate stations. Because contamination can cause stepper hot spots or further contamination of process tools, it is desirable to detect contamination before it creates further problems.

Therefore, it is desirable to provide a system and method that is better able to detect contamination and defects, as well as provide for improved review of wafers.

SUMMARY OF THE INVENTION

In various embodiments, the invention provides methods and systems for review of semiconductor wafers. In one embodiment, a method is provided that comprises downloading front side inspection data for the wafer from a control computer to a review station and positioning the wafer in response to the front side inspection data. The front side of the wafer is reviewed. The wafer is inverted, and back side inspection data for the wafer is downloaded from the control computer to the review station. The wafer is positioned in response to the back side inspection data, and the back side of the wafer is reviewed.

In another embodiment, a wafer review method comprises downloading front side inspection data for the wafer from a control computer to a first review station and positioning the wafer at the first review station in response to the front side inspection data. The wafer is reviewed and then moved to a second review station. The wafer is inverted, and back side inspection data for the wafer is downloaded from the control computer to the second review station. The wafer is then positioned at the second review station in response to the back side inspection data and thereafter reviewed.

In another embodiment, a semiconductor wafer review system is provided. The system comprises a robotic arm arranged to retrieve a wafer from a cassette. A wafer inverter is arranged to receive a wafer from the robotic arm, and a wafer transfer mechanism is arranged to receive the wafer from the wafer inverter and move the wafer. A microscope review station is arranged to receive the wafer from the wafer transfer mechanism and position the wafer for review with an objective.

A semiconductor wafer analysis system is provided in another embodiment. The system comprises a manufacturing control system arranged to transmit inspection data. A first review station is coupled to the control system and equipped with a microscope. The first review station is further arranged to receive wafer inspection data from the control system. A second review station is coupled to the control system and equipped with a microscope, and further arranged to receive inspection data from the control system. A wafer inverter is configured with the second review station and arranged to flip a wafer to be reviewed with the microscope of the second review station, whereby the backside of the wafer is exposed for viewing.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of semiconductor transistor arrangements. The invention has been found to be particularly advantageous in applications such as PMOS, NMOS, CMOS, BiCMOS, and Bipolar devices. While the present invention is not so limited, an appreciation of various aspects of the invention is best gained through a discussion of various application examples of processes used to form such semiconductor devices.

Figure 1:
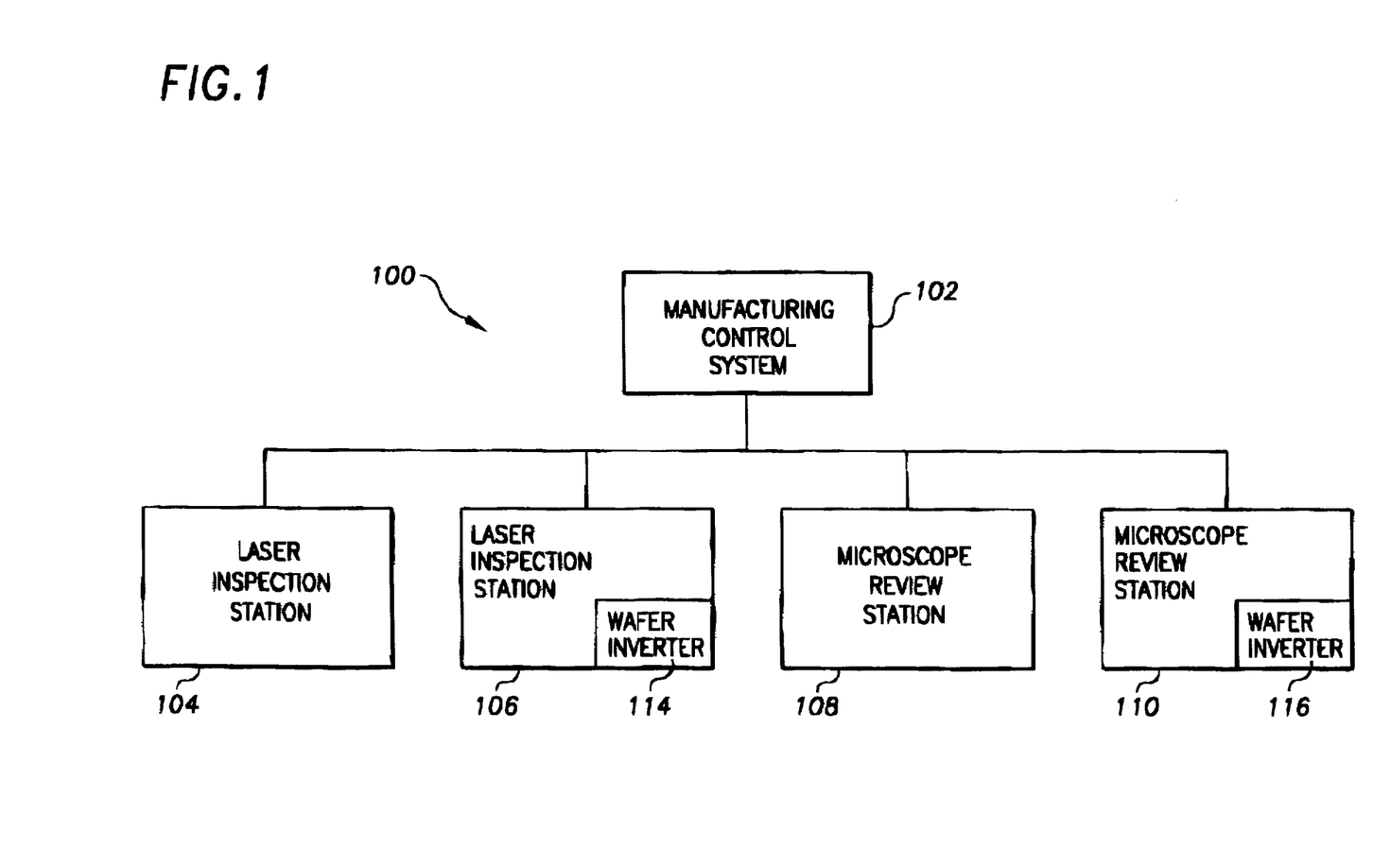
FIG. 1 is a block diagram of a system for inspection and review of semiconductor wafers according to an example embodiment of the invention.

FIG. 1 is a block diagram of a system 100 for inspection and review of semiconductor wafers according to an example embodiment of the invention. The system 100 includes a manufacturing control system 102, a pair of laser inspection stations 104 and 106, and a pair of microscope review stations 108 and 110. Cassettes carrying wafers are moved between the stations 104–110 by hand. It will be appreciated that laser inspection and microscope review stations in addition to stations 104–110, as well as other types of stations, could be provided in system 100.

The stations 104–110 are coupled to the manufacturing control system 102. In an example embodiment, and the manufacturing control system includes Workstream software that is available from Consilium, along with suitable hardware. The laser inspection station 106 and microscope review station 110 are equipped with respective wafer inverters 114 and 116, which, in an example embodiment, flip a wafer to expose its back side for laser inspection or microscope review. The wafer inverters 114 and 116 configured with the respective laser inspection station 106 and microscope review station 110 permit analysis of the back side of a semiconductor wafer.

In an example scenario, an operator loads a cassette of wafers into the inspection station 104. In an example embodiment, the laser inspection station is an argon ion laser scanner such as the A17 station that is available from KLA Tencor. One-by-one, either all or selected ones of the wafers in the cassette are removed from the cassette, staged for laser scanning, and laser scanned. Laser scanned data for the wafers is returned to the control system 102 or another suitable defect database. For example, the data may include the coordinates on the wafer at which reflected laser light having certain characteristics is detected. In an example embodiment, the characteristics are indicative of a defect. Thus, at laser inspection station 104, front side laser inspection data is gathered.

After laser scanning the front sides of the wafers, the cassette is moved to second laser inspection station 106. The laser inspection station 106 is configured with the wafer inverter 114, whereby the wafers are flipped in order to collect laser scan data for the back sides of the wafers. Operation of and processing by the laser inspection station 106 is similar to that of laser inspection station 104. However, before a wafer is staged and laser scanned, the wafer inverter flips the wafer to expose its back side for laser scanning. The laser inspection station transmits back side inspection data to the manufacturing control system 102. After the wafers have been processed by laser inspection stations 104 and 106, the manufacturing control system 102 has received both front side and back side inspection data for the wafers.

The cassette of wafers it then moved to the microscope review station 108 for visual review of selected areas of the wafers. For example, if for a particular wafer the front side inspection data indicates that a defect may be present at a certain coordinate, it is desirable to visually review the defect area and judge whether the defect makes the wafer unusable. As such, the front side inspection data for the wafer, is transmitted to the microscope review station 108. The microscope review station 108, in response to the front side inspection data, positions the wafer under the microscope to permit viewing of the defect. Without the coordinates, the operator would be left having to manually position the wafer for viewing the defect, which is virtually impossible. In an example embodiment, the microscope review station is an INS 3000 that is available from Leica.

For wafers that are acceptable after having reviewed the front sides, visual inspection of the back sides of the wafers is desirable to review the back side defects. The cassette of wafers is moved to the second microscope review station 110. Each wafer selected for visual review and prior to being staged under the microscope of station 110, is flipped by wafer inverter 116 in order to expose the back side of the wafer to the microscope. The back side inspection data is transmitted from the control system 102 to the review station 110, and the review station positions each wafer under the microscope in response to the back side inspection data.

While the embodiment of FIG. 1 shows the front side and back side inspections and reviews being performed on separate stations, in another embodiment, both the front side and back side inspection could be performed on the same laser scanning station, and both the front side and back side review could be performed on the same microscope review station. The illustrated embodiment is believed to be beneficial in arrangements already having conventional inspection and review stations for analyzing the front sides of wafers.

Figure 2:
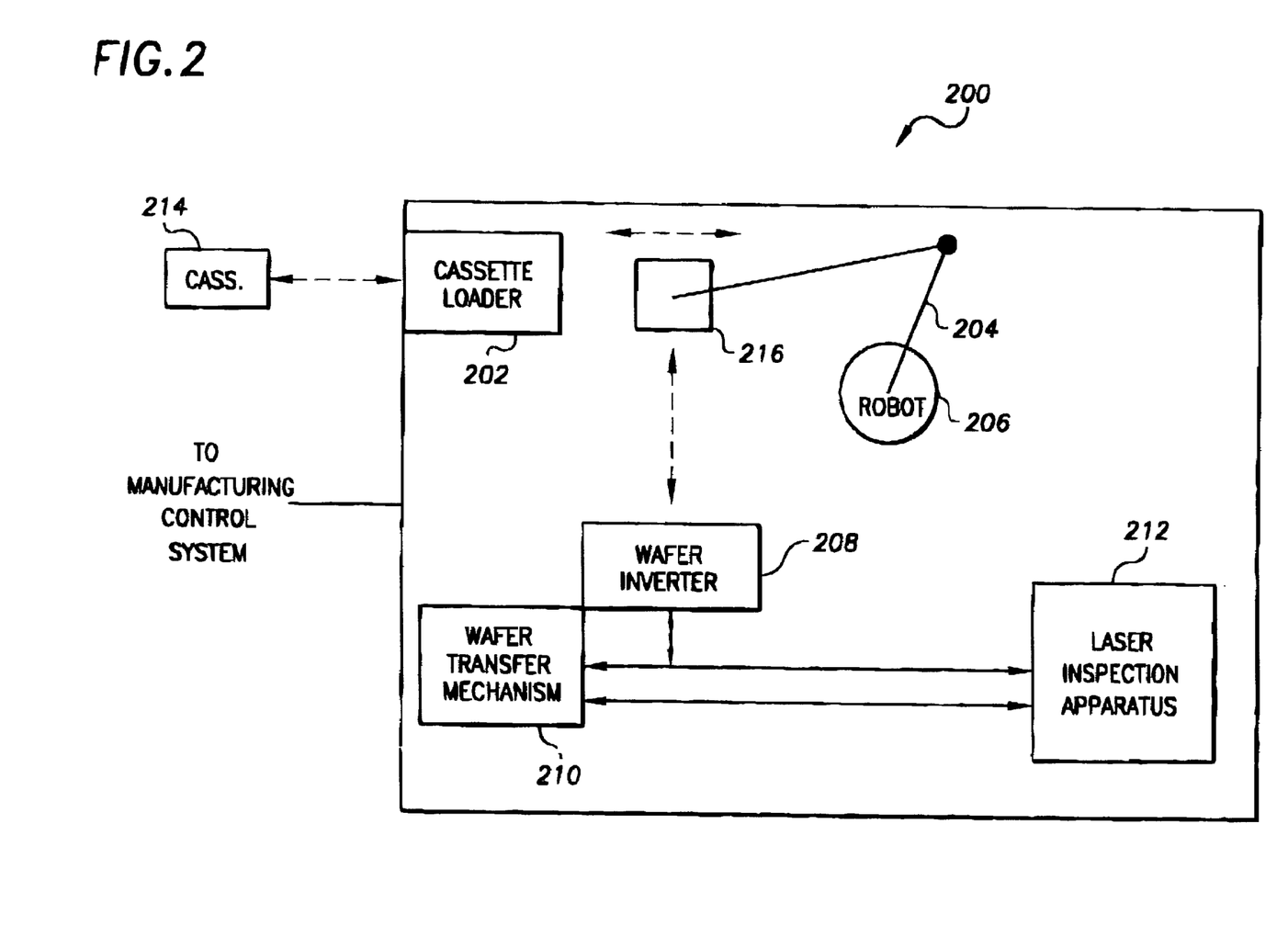
FIG. 2 is a block diagram of a laser inspection station equipped with a wafer inverter in accordance with an example embodiment of the invention.

FIG. 2 is a block diagram of a laser inspection station 200 equipped with a wafer inverter in accordance with an example embodiment of the invention. The station includes a cassette loader, an arm 204 controlled by robot 206, a wafer inverter 208, a wafer transfer mechanism 210, and a laser inspection apparatus 212. The various components of the station 200 are coupled to the manufacturing control system 102.

The station 200 includes a cassette loader 202 that is arranged to receive a cassette 214. The cassette loader 202 is present on the aforementioned INS 3000 inspection station, according to an example embodiment. The robot 206 controls the arm 204 to remove a wafer from a cassette in the cassette loader 202 and move the wafer to the wafer inverter 208. In an example embodiment, the arm 204 has a vacuum paddle 216 for lifting a wafer. In an alternative embodiment, the arm 204 includes Teflon coated edge grippers that support the wafer in removing the wafer from the cassette and moving the wafer to the wafer inverter 208.

The wafer inverter 208 receives the wafer from the arm 204 and flips the wafer to expose the back side of the wafer. In an alternative embodiment, the robot and arm 204 could be adapted to invert the wafer, for example, as described in U.S. Pat. No. 5,105,147 to Karasikov et al. entitled, WAFER INSPECTION SYSTEM, which is hereby incorporated by reference. In yet another embodiment, the wafer inverter 208 could be adapted to let a wafer pass through without inverting it, thereby permitting both front side and back side laser inspection by the same station 200. The wafer inverter 208 provides the wafer to the wafer transfer mechanism 210, which moves and stages the wafer for the laser inspection apparatus 212.

Various examples of inspection stations, cassette loaders, robots, wafer inverters, wafer transfer mechanisms, and laser inspection apparatus are described in U.S. Pat. No. 5,578,821 to Meisberger et al. entitled, ELECTRON BEAM INSPECTION SYSTEM AND METHOD; U.S. Pat. No. 5,640,237 to Esrig et al. entitled, METHOD AND APPARATUS FOR DETECTING NON-UNIFORMITIES IN REFLECTIVE SURFACES; U.S. Pat. No. 5,765,890 to Gaylord et al. entitled, DEVICE FOR TRANSFERRING A SEMICONDUCTOR WAFER; U.S. Pat. No. 4,775,281 to Prentakis entitled, APPARATUS AND METHOD FOR LOADING AND UNLOADING WAFERS; U.S. Pat. No. 5,647,718 to Wiesler et al. entitled, STRAIGHT LINE WAFER TRANSFER SYSTEM; U.S. Pat. No. 4,618,938 to Sandland et al. entitled, METHOD AND APPARATUS FOR AUTOMATIC WAFER INSPECTION; and U.S. Pat. No. 4,938,654 to Schram entitled, AUTOMATED WAFER INSPECTION SYSTEM; all of which are hereby incorporated by reference.

Figure 3:
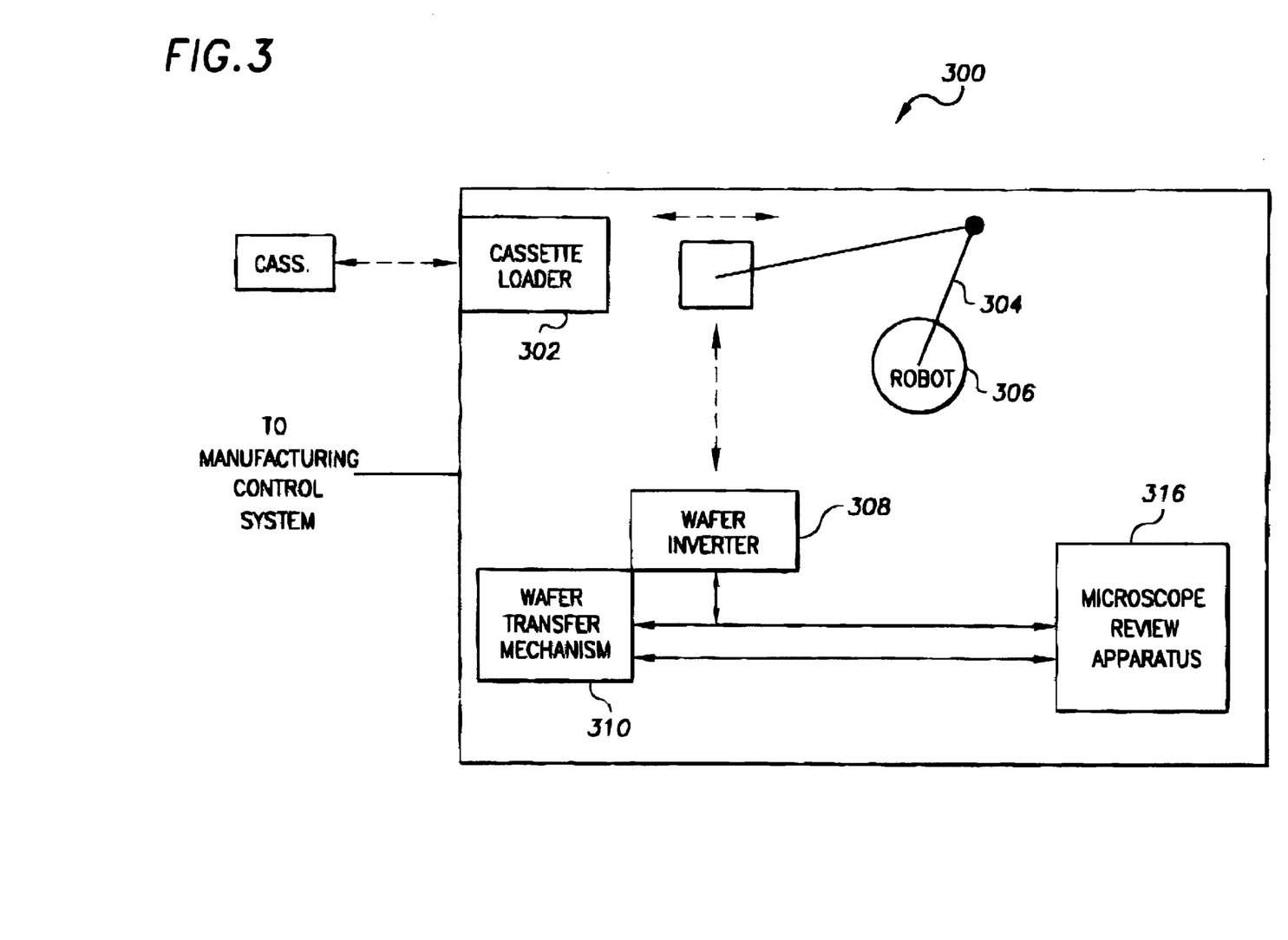
FIG. 3 is a block diagram of a microscope review station configured with a wafer inverter according to an example embodiment of the invention.

FIG. 3 is a block diagram of a microscope review station 300 configured with a wafer inverter 308 according to an example embodiment of the invention. The example station 300 can include the same supporting apparatus found in the laser inspection station 200 of FIG. 2. That is, the cassette loader 302, robot 306 and arm 304, wafer inverter 308, and wafer transfer mechanism 310 may be comparable to the corresponding apparatus of the laser inspection station 200. However, it will be appreciated that the various apparatus may require adaptation to function with the microscope review apparatus 316.

Figures 4, 4A:
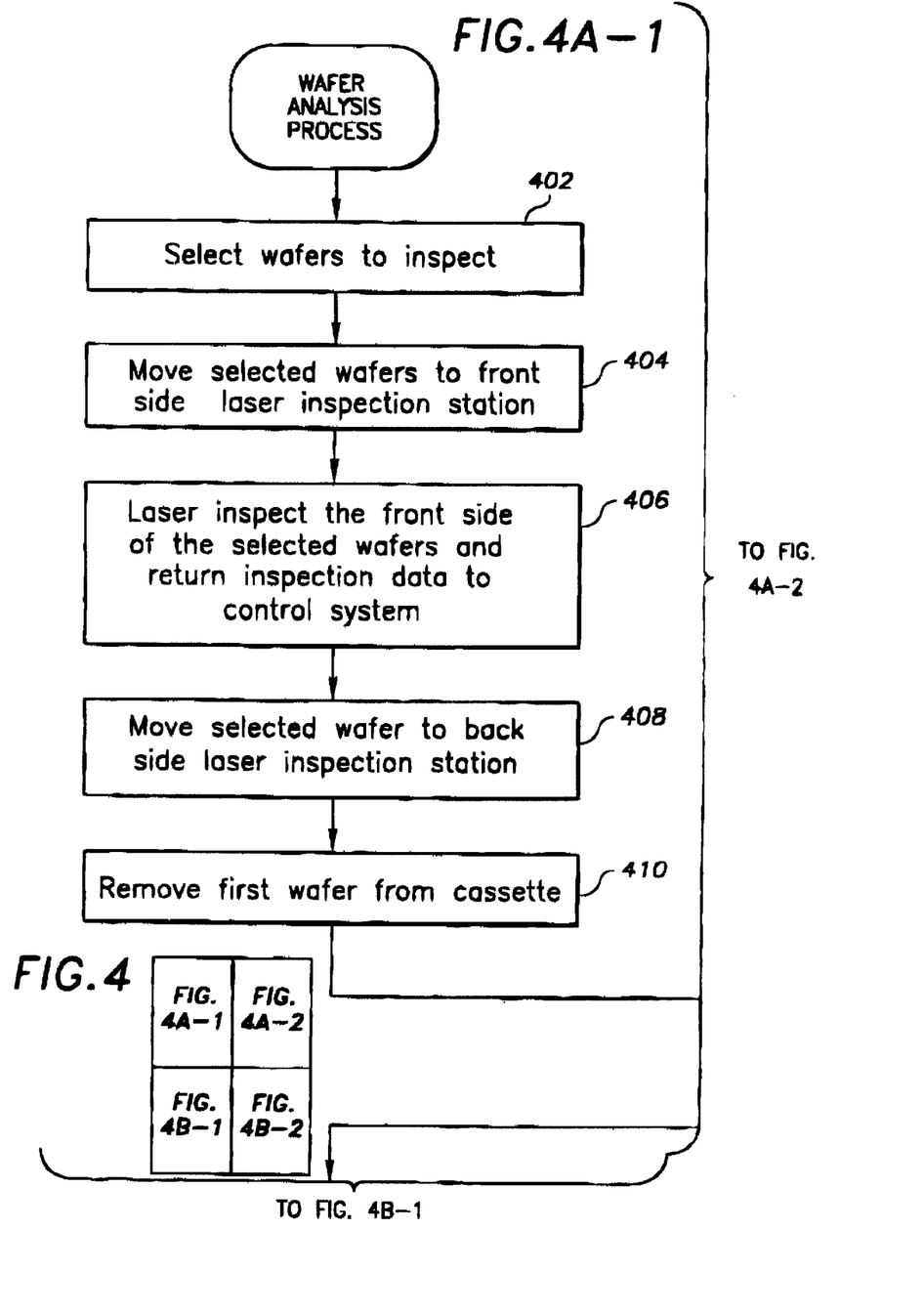
FIG. 4A is a portion of a flowchart of a process for analyzing wafers, according to an example embodiment of the present invention.
FIG. 4B is a continuation of the flowchart of FIG. 4A.
Figure 4A:
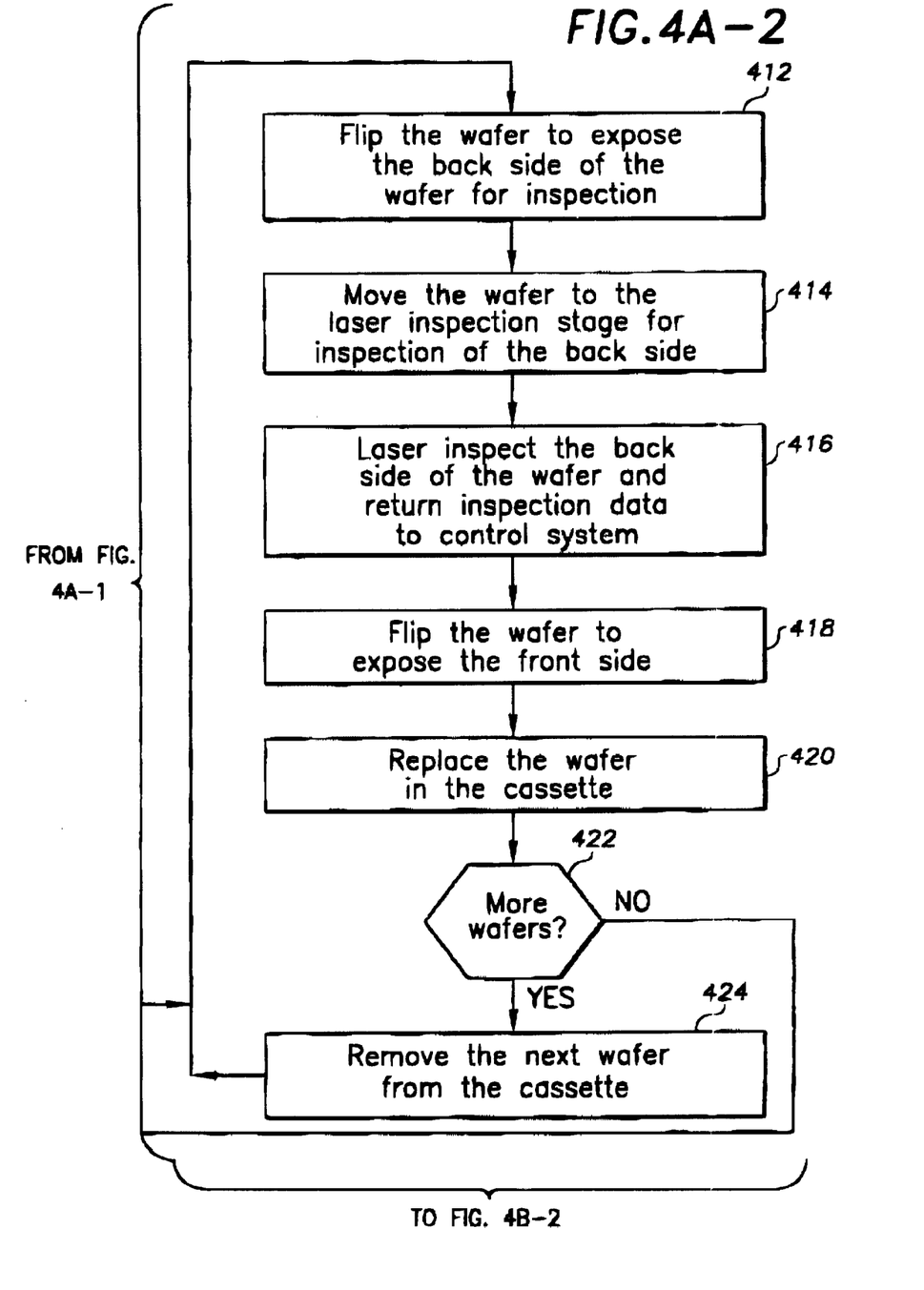
Figure 4B:
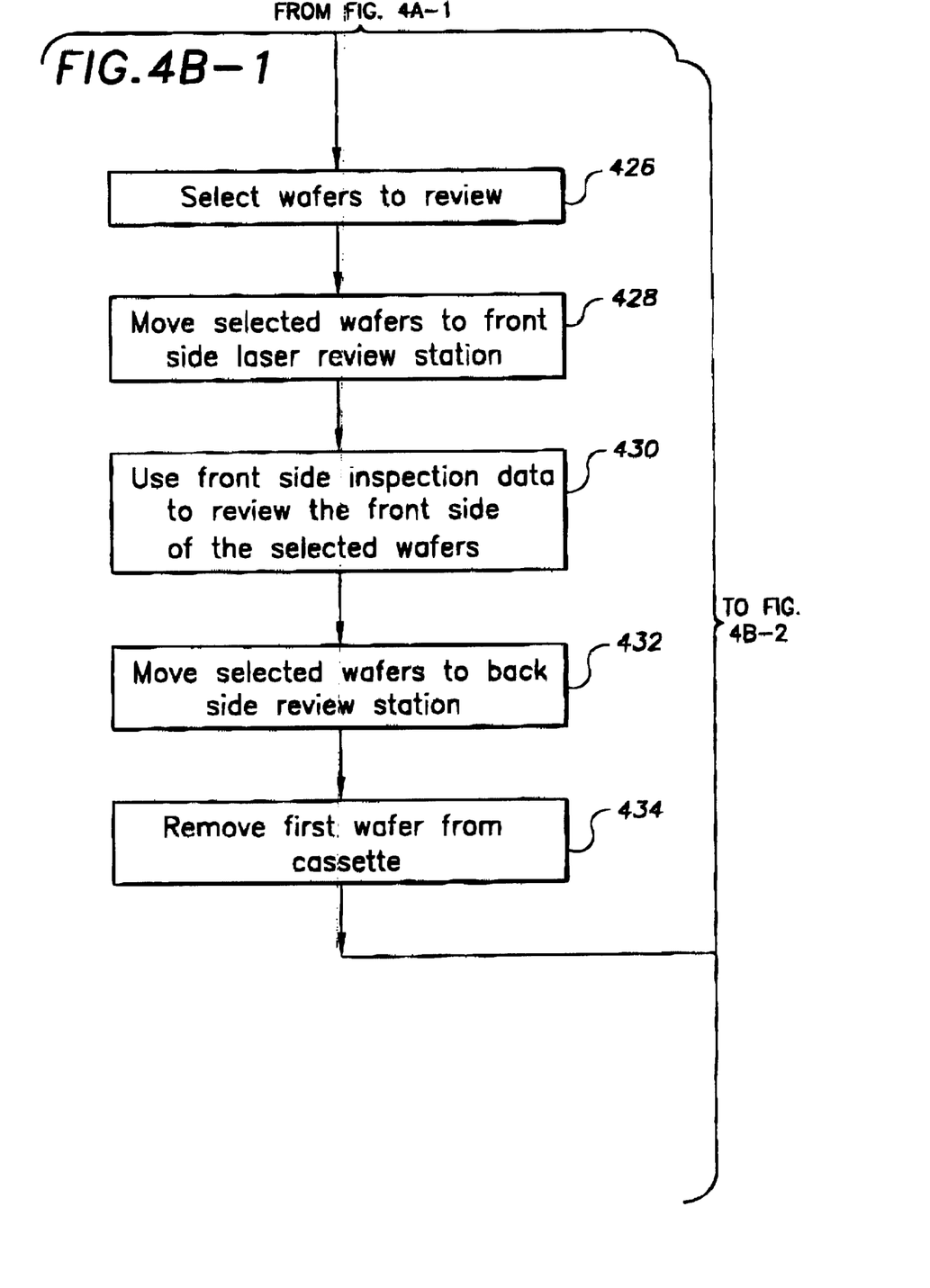
Figure 4B:
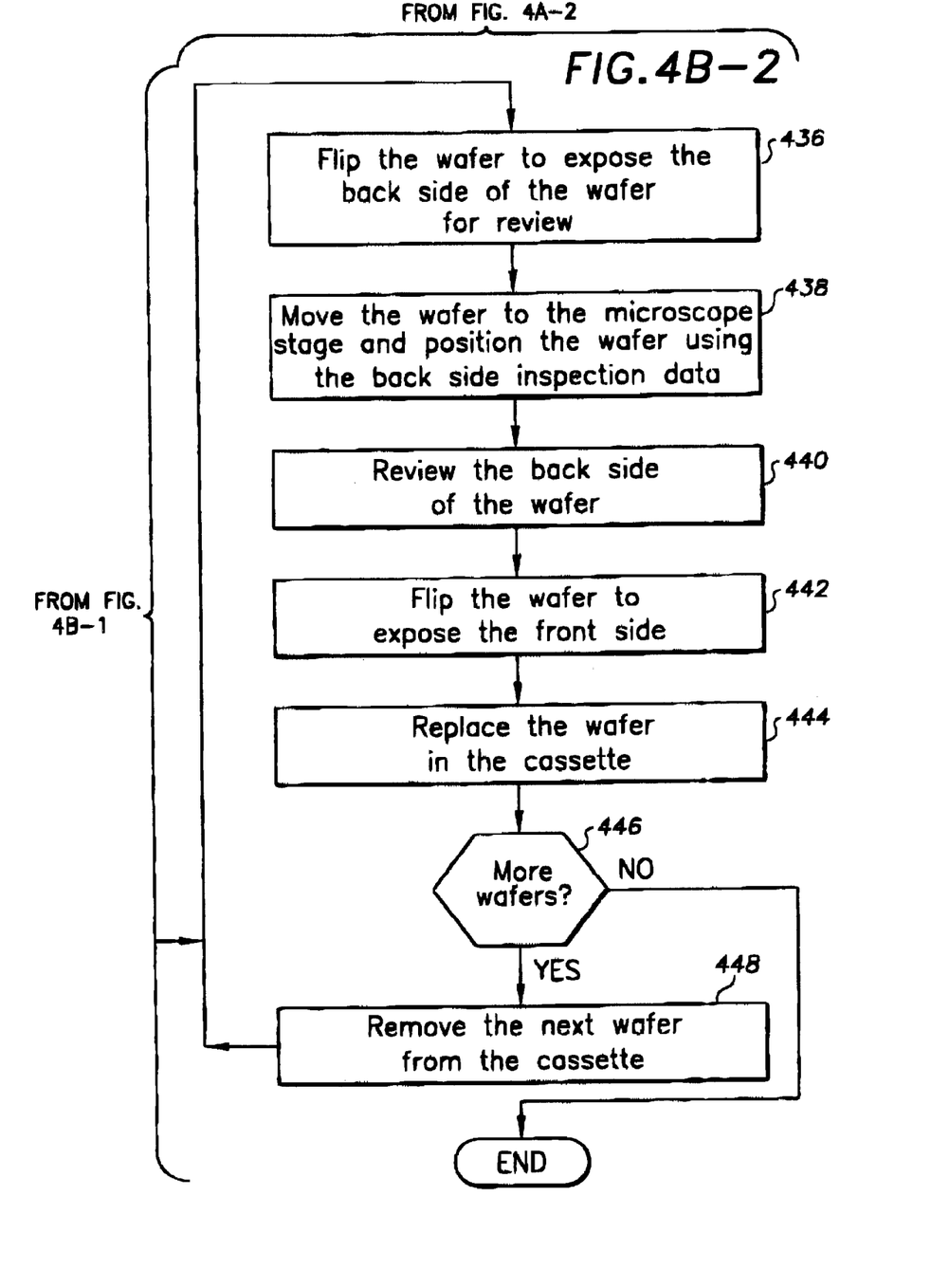

FIG. 4 shows the relationship between FIGS. 4A and 4B, which together comprise a flowchart of a process for analyzing wafers according to various example embodiments of the invention. Generally, the example process sequence involves laser scanning the front sides of wafers, laser scanning the back sides of wafers, reviewing the front sides of wafers, and reviewing the back sides of wafers. In one embodiment, both the front side inspection and front side review of the wafers are performed with convention equipment. In another embodiment, both the front side and back side inspection could be performed on the same laser scanning station, and both the front side and back side review could be performed on the same microscope review station.

The first phase of the process sequence includes steps 402, 404, and 406 where the front sides of selected wafers are laser scanned. The laser scanning is performed at conventional laser scanning stations, and front side inspection data is returned to a control system.

The wafers are then moved (step 408) to a back side laser inspection station, for example, station 200 of FIG. 2. Process steps 410–424 illustrate example processing performed to laser scan the back sides of the wafers. A wafer is first removed from the cassette (step 410) and then flipped to expose the back side for laser scanning (step 412). At step 414, the wafer is moved to the laser inspection stage for laser scanning the back side. The back side inspection data, which varies by type of inspection station, is transmitted at block 416 to the control system for subsequent usage. Having laser scanned the back side of the wafer, the wafer is again flipped to return the wafer to having its front side exposed (upwards, for example) and replaced in the cassette, as shown by blocks 418 and 420. While there are wafers in the cassette that have not been back side laser scanned, steps 422 and 424 continue the process of laser scanning the back sides of the wafers.

When all the wafers have had their back sides laser scanned, step 422 directs control to step 426 of FIG. 4B where wafers are selected for visual review. The selection may be made based on the reflected image of a laser scanned wafer possessing certain characteristics indicative of defects. The selected wafers are moved to a front side microscope review station at step 428, and at step 430 the selected wafers are reviewed. Front side inspection data is transmitted from the control system to the front side review station for the purpose of positioning the wafers under the microscope to view the defects.

At step 432, selected wafers are moved to the back side microscope review station. The criteria for selecting the wafers may include certain characteristics that are present in the reflected image of the back side of a wafer when subjected to laser scanning. It will be appreciated that, as with the laser scanning station configured with the wafer inverter, the microscope review station that is configured with a wafer inverter may be adapted for review of both the front side and the back side of a wafer. Thus, the step 432 of moving the wafers to a back side microscope review station is not required in all embodiments.

The first selected wafer is removed from the cassette at step 434, and at step 436 the wafer is flipped to expose the back side for review with a microscope. The wafer is then moved to the microscope stage, and using the back side inspection data transmitted from the control system, the wafer is positioned under the microscope to provide a view of a selected defect, as shown by step 438. After the back side of the wafer is reviewed at step 440, the wafer is again flipped to return it to having its front side exposed at step 442. The wafer is then replaced in the cassette at step 444, and steps 446 and 448 continue the process of back side review until all the selected wafers have been processed.

Figure 5:
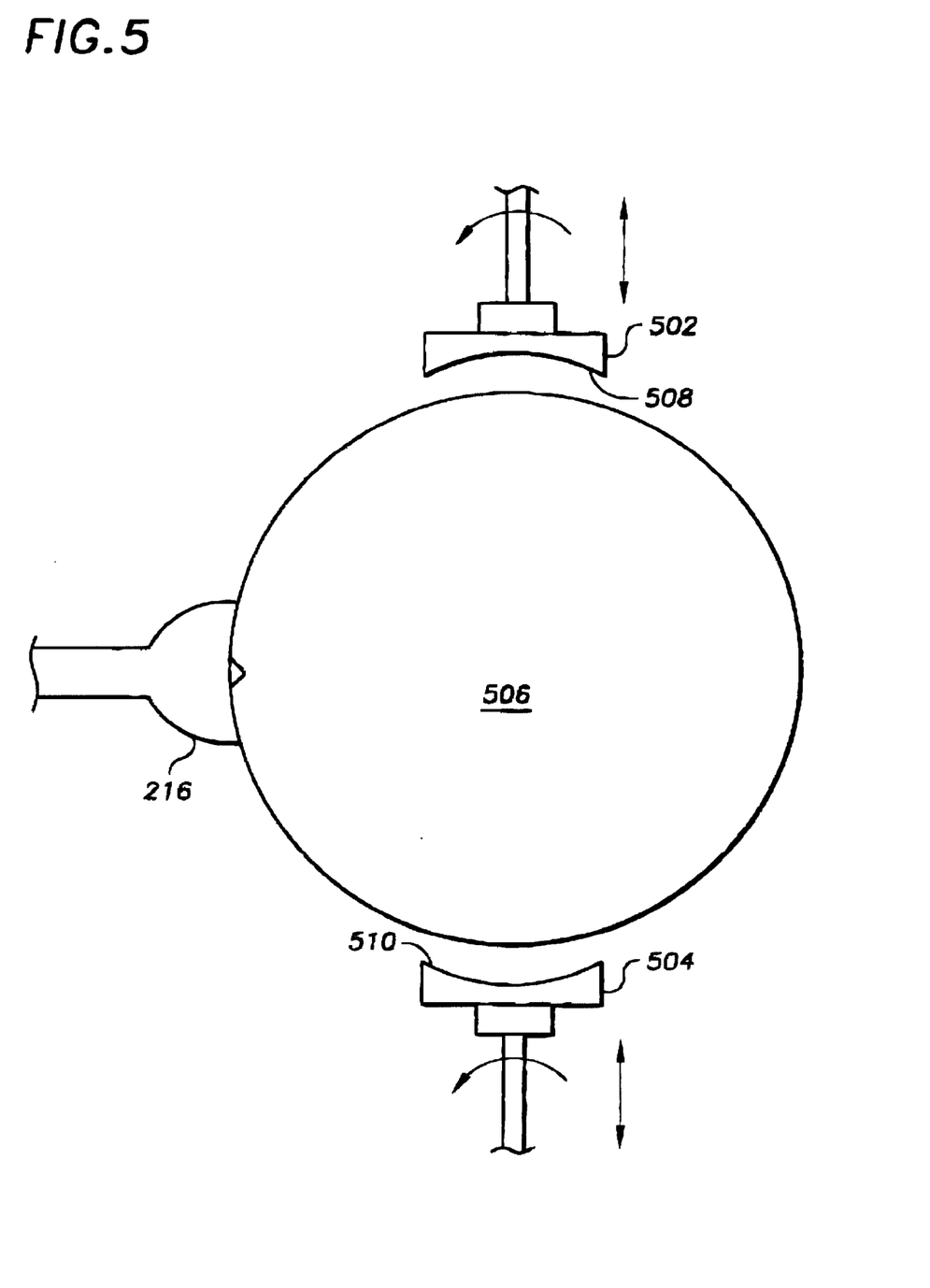
FIG. 5 is a semiconductor wafer handler, according to an example embodiment of the present invention.

FIG. 5 is a partial view of an example embodiment of a wafer inverter 208. The inverter 208 includes two clamps 502 and 504 that are arranged to contact and grip the wafer 506. In an example embodiment, the gripper portions 508 and 510 are Teflon® coated. It will be appreciated that the gripper portions could be alternatively coated with material having characteristics similar to Teflon.

The wafer 506 is delivered to the inverter 208 by the robot 206 (FIG. 2), and the wafer inverter positions clamps 502 and 504 to grip the wafer. The robot 206 then releases the wafer 506 from the vacuum paddle 216. In response to user controls or a programmed sequence, the wafer inverter 208 rotates the wafer 506 180°. Depending upon the desired process sequence, the wafer 506 may or may not be rotated by the wafer inverter. For example, when the front side of a wafer is to be inspected, no rotation is required. Whereas, when the backside is to be inspected, the wafer is rotated. In addition, when a wafer is to be returned to a cassette after having had its backside inspected, the wafer is preferably rotated back to having its front side facing up.

Figure 6:
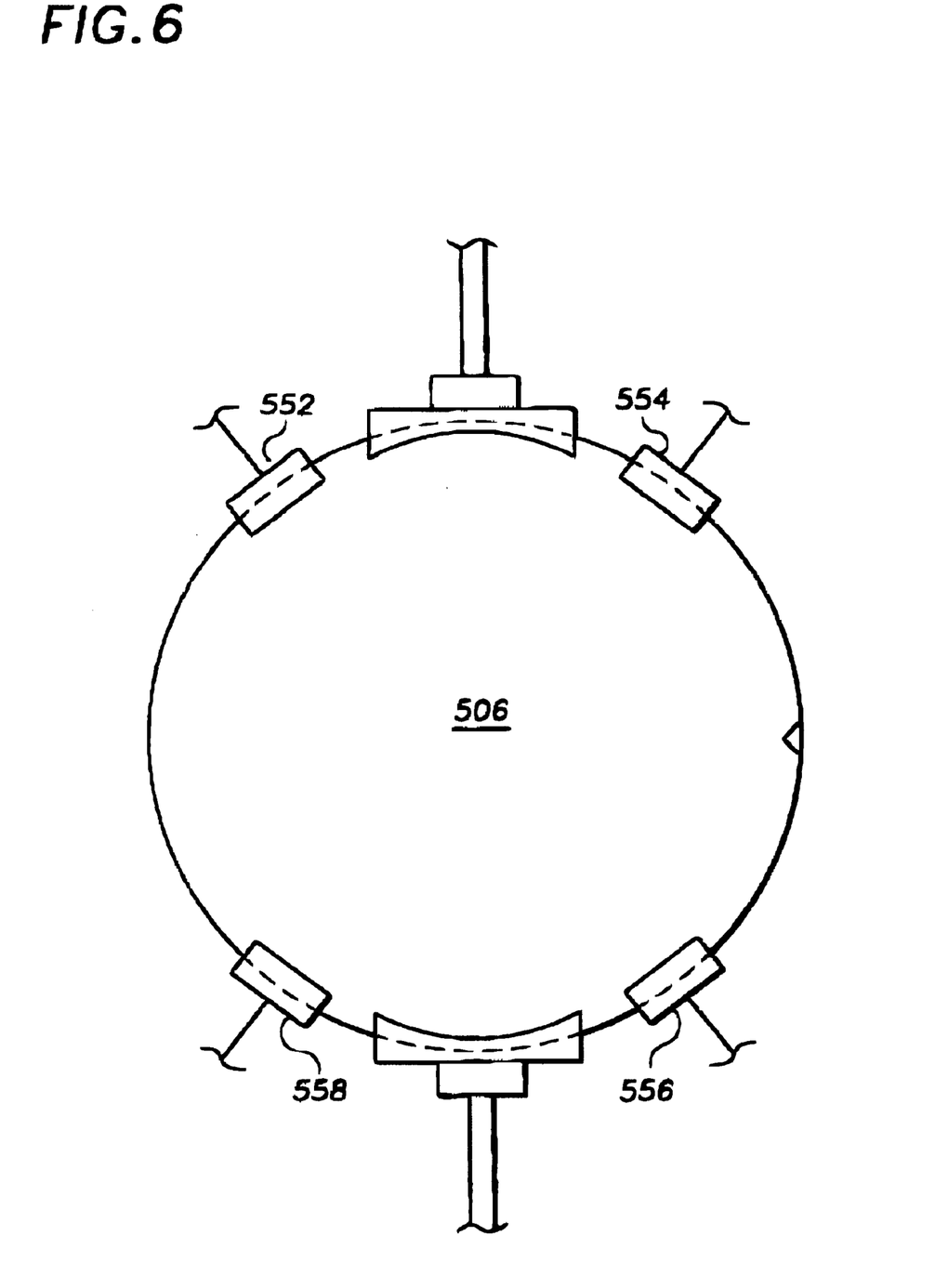
FIG. 6 is a semiconductor wafer handler, according to another example embodiment of the present invention.
Figure 7:
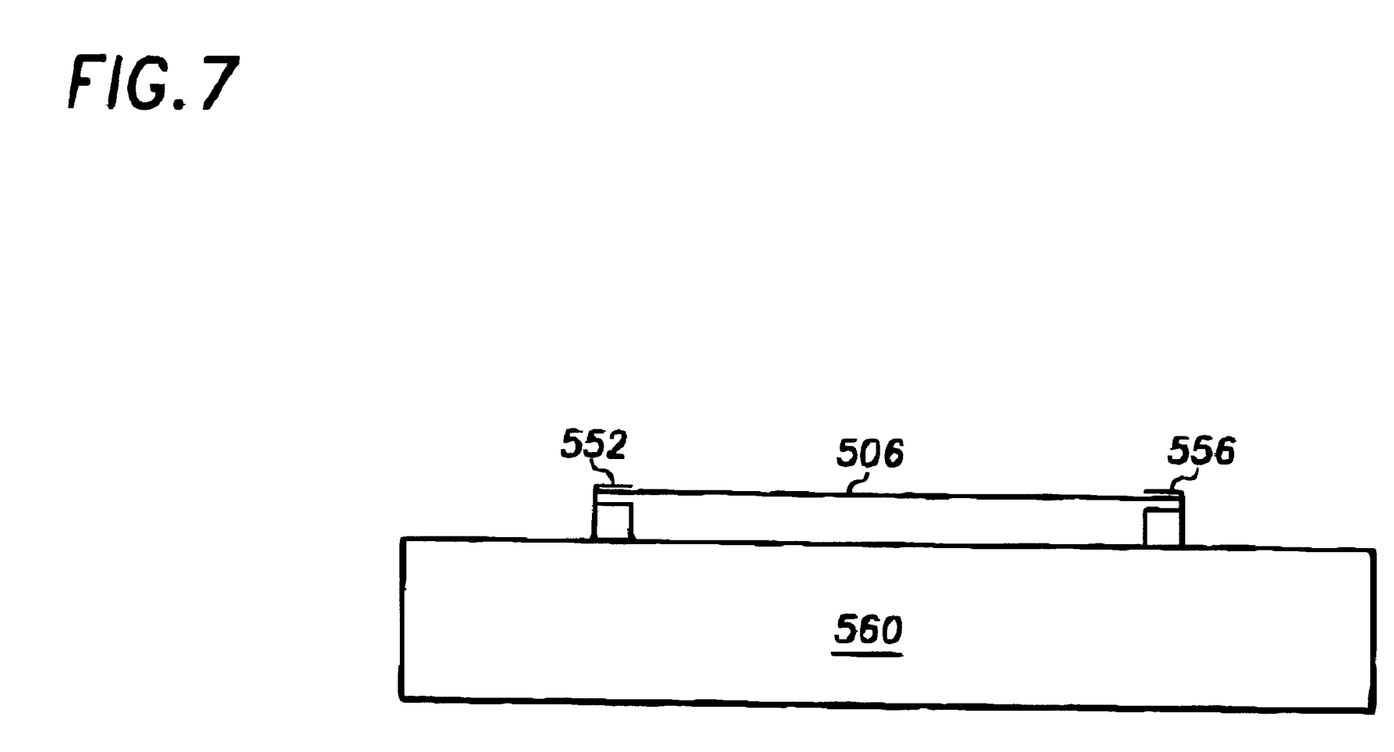
FIG. 7 is a semiconductor wafer stage, according to another example embodiment of the present invention.

Turning now to FIGS. 6 and 7, an example embodiment is illustrated in which a wafer inverter positions the wafer 506 for engagement by stage clamps 552, 554, 556, and 558. The stage clamps 552–558 are conventional components arranged for use with an inspection or review station 212 or 316. The stage clamps are coated with a Teflon-type material and are arranged to stabilize the wafer 506 for inspection or review. The stage clamps 552–558 are supported by a conventional stage 560, and a microscope objective (not shown) or laser scanner (not shown) is positioned above the wafer 506 for viewing or scanning the wafer. The clamps 552–558, as well as the clamps 502 and 504 of FIG. 5, are made to minimize contact with the front side and back side surfaces of the wafer 506.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art upon review of the present specification. The claims are intended to cover such modifications and devices.

What is claimed is:

1. A method for review of a semiconductor wafer having a front side and a back side, the method comprising:
    positioning the wafer in response to front side wafer inspection data;
    after positioning the wafer, reviewing the front side of the wafer;
    inverting the wafer and exposing a back side of the wafer for review;
    positioning the inverted wafer in response to back side wafer inspection data; and
    reviewing the back side of the inverted wafer.

2. The method of claim 1, further comprising inverting the wafer after reviewing the back side.

3. The method of claim 1, further comprising performing the review of the semiconductor wafer in a system comprising a control computer and a review station.

4. The method of claim 3, further comprising downloading front side inspection data for the wafer from the control computer to the review station.

5. The method of claim 4, further comprising downloading back side inspection data for the wafer from the control computer to the review station.

6. The method of claim 1, wherein positioning the wafer includes using a robotic arm adapted to position the wafer.

7. The method of claim 6, further comprising adapting the robotic arm with a vacuum paddle adapted to hold the wafer using the vacuum.

8. The method of claim 3, further comprising adapting the vacuum paddle to rotate, wherein positioning the wafer includes rotating the vacuum paddle.

9. The method of claim 1, further comprising clamping the wafer with at least two clamps, prior to reviewing the wafer.

10. The method of claim 1, further comprising using a microscope and analyzing the wafer.

11. A method for review of a semiconductor wafer in a computer controlled wafer analysis system including at least two review stations, comprising the steps of:
    downloading front side inspection data for the wafer from a control computer to a first one of the review stations;
    positioning the wafer at the first review station in response to the front side inspection data;
    reviewing the front side of the wafer with a microscope;
    moving the wafer to a second one of the review stations;
    inverting the wafer, whereby a back side of the wafer is exposed for review;
    downloading back side inspection data for the wafer from the control computer to the second review station;
    positioning the wafer at the second review station in response to the back side inspection data; and
    reviewing the back side of the wafer with a microscope.

12. The method of claim 11, further comprising inverting the wafer after reviewing the back side.

13. The method of claim 12, further comprising:
    (a) moving a cassette containing a plurality of wafers to the first review station;
    (b) removing a selected one of the wafers from the cassette;
    (c) replacing the wafer in the cassette after reviewing the front side;
    repeating steps (a)–(c) until front sides of the wafers have been reviewed;
    (d) moving the cassette to the second review station;
    (e) removing a selected one of the wafers from the cassette;
    (g) replacing the wafer in the cassette after reviewing the back side; and
    repeating steps (d)–(f) until back sides of the wafers have been reviewed.

14. A method for review of a semiconductor wafer having a front side and a back side, the method comprising:
    positioning the wafer in response to front side wafer inspection data including positioning the wafer at a first review station;
    after positioning the wafer, reviewing the front side of the wafer;
    inverting the wafer and exposing a back side of the wafer for review;
    positioning the inverted wafer in response to back side wafer inspection data including positioning the wafer at a second review station;
    moving the wafer between the first and second review stations; and
    reviewing the back side of the inverted wafer;
    wherein the semiconductor wafer is reviewed in a system comprising a control computer and a review station.

15. A method for review of a semiconductor wafer having a front side and a back side, the method comprising:
    downloading front side inspection data for the wafer from a control computer to a first review station;
    retrieving the wafer with a robotic arm having a vacuum paddle, the vacuum paddle being adapted to hold the wafer with vacuum suction;
    in response to the front side inspection data, positioning the wafer in the first review station with the robotic arm and clamping the wafer in position;
    reviewing the front side of the wafer with a microscope;
    retrieving the wafer from the first review station with the robotic arm;
    downloading back side inspection data for the wafer from the control computer to a second review station;
    in response to the back side inspection data, inverting the wafer and positioning the wafer in the second review station and clamping the wafer in position, whereby a back side of the wafer is exposed for review; and
    reviewing the back side of the wafer with a microscope.

16. A system for review of a semiconductor wafer having a front side and a back side, the system comprising:
    means for positioning the wafer in response to front side wafer inspection data;
    means for reviewing the front side of the wafer after it has been positioned;
    means for inverting the wafer and exposing a back side of the wafer for review;
    means for positioning the inverted wafer in response to back side wafer inspection data; and
    means for reviewing the back side of the inverted wafer.

17. The system of claim 16, further comprising:
    means for downloading the front side inspection data from a control computer to the means for positioning the wafer in response to front wafer inspection data; and means for downloading the back side inspection data from a control computer to the means for positioning the wafer in response to back side wafer inspection data.

18. A method for review of a semiconductor wafer having a front side and a back side, the method comprising:
    positioning the wafer at a first review station in response to front side wafer inspection data;
    after positioning the wafer at the first review station, using a system comprising a control computer and the first review station and reviewing the front side of the wafer;
    inverting the wafer and exposing a back side of the wafer for review;
    moving the wafer from the first review station to a second review station;
    positioning the inverted wafer at the second review station in response to back side wafer inspection data; and
    using a system comprising a control computer and the second review station and reviewing the back side of the positioned inverted wafer.

19. A method for review of a semiconductor wafer having a front side and a back side, the method comprising:
    clamping the wafer with at least two clamps;
    positioning the wafer in response to front side wafer inspection data;
    after positioning the clamped wafer, reviewing the front side of the wafer;
    inverting the wafer and exposing a back side of the wafer for review;
    positioning the inverted wafer in response to back side wafer inspection data; and
    reviewing the back side of the inverted wafer.

20. A system for review of a semiconductor wafer in a computer controlled wafer analysis system including at least two review stations, the system comprising:
    means for downloading front side inspection data for the wafer from a control computer to a first one of the review stations;
    means for positioning the wafer at the first review station in response to the front side inspection data;
    means for reviewing the front side of the positioned wafer with a microscope;
    means for moving the wafer to a second one of the review stations;
    means for inverting the wafer and exposing a back side of the wafer for review;
    means for downloading back side inspection data for the wafer from the control computer to the second review station;
    means for positioning the inverted wafer at the second review station in response to the back side inspection data; and
    means for reviewing the back side of the wafer with a microscope.

21. A system for review of a semiconductor wafer in a computer controlled wafer analysis system including at least two review stations, the system comprising:
    a control system adapted to download front side inspection data for the wafer from a control computer to a first one of the review stations;
    a positioning arrangement adapted to position the wafer at the first review station in response to the front side inspection data;
    a front side reviewing arrangement adapted to review the front side of the positioned wafer with a microscope;
    a moving arrangement adapted to move the wafer to a second one of the review stations;
    an inverting arrangement adapted to invert the wafer and expose a back side of the wafer for review;
    a control system adapted to download back side inspection data for the wafer from the control computer to the second review station;
    a positioning arrangement adapted to position the inverted wafer at the second review station in response to the back side inspection data; and
    a back side reviewing arrangement adapted to review the back side of the inverted wafer with a microscope.

22. The system of claim 21, wherein the positioning arrangement includes a robotic arm arranged to retrieve a wafer from a cassette, wherein the inverting arrangement includes a wafer inverter arranged to receive a wafer from the robotic arm and to flip the wafer, wherein the moving arrangement includes a wafer transfer mechanism arranged to receive the wafer from the wafer inverter and move the wafer, and wherein the front side reviewing arrangement includes a microscope review station arranged to receive the wafer from the wafer transfer mechanism and position the wafer for review with an objective.

23. The system of claim 21, wherein the control system is arranged to transmit inspection data, wherein the front side reviewing arrangement includes a first review station coupled to the control system, equipped with a microscope, and arranged to receive wafer inspection data from the control system, wherein the back side reviewing arrangement includes a second review station coupled to the control system, equipped with a microscope, and arranged to receive inspection data from the control system, and wherein the inverting arrangement includes a wafer inverter configured with the second review station and arranged to flip a wafer to be reviewed with the microscope of the second review station, whereby the backside of the wafer is exposed for viewing.

24. The system of claim 21, wherein at least one of the positioning arrangements includes a robotic arm.

25. The system of claim 21, wherein the robotic arm is adapted to retrieve a wafer from a cassette.

26. The system of claim 24, wherein the robotic arm is equipped with a vacuum paddle.

27. The system of claim 26, wherein the vacuum paddle is adapted to hold the wafer.

28. The system of claim 24, wherein the inverting arrangement includes a wafer inverter adapted to receive the wafer from the robotic arm.

29. The system of claim 21, wherein at least one of the reviewing arrangements includes a stage, wherein the positioning arrangements are adapted to position the wafer on the stage.

* * * * *

UNITED STATES PATENT AND TRADEMARK OFFICE
CERTIFICATE OF CORRECTION

PATENT NO.     : 6,401,008 B1
DATED          : June 4, 2002
INVENTOR(S)    : Ehrichs et al.

It is certified that error appears in the above-identified patent and that said Letters Patent is hereby corrected as shown below:

<u>Column 7,</u>
Lines 26 and 34, "method of claim 3" should read -- method of claim 7 --.

Signed and Sealed this

Eleventh Day of February, 2003

JAMES E. ROGAN
*Director of the United States Patent and Trademark Office*